United States Patent [19]

Yale et al.

[11] 4,022,897
[45] May 10, 1977

[54] CNS ACTIVE COMPOUNDS

[75] Inventors: Harry Louis Yale, New Brunswick; John T. Sheehan, Middlesex, both of N.J.

[73] Assignee: E. R. Squibb & Sons, Inc., Princeton, N.J.

[22] Filed: Apr. 17, 1975

[21] Appl. No.: 569,132

Related U.S. Application Data

[63] Continuation-in-part of Ser. No. 448,133, March 4, 1974, abandoned, which is a continuation-in-part of Ser. No. 181,565, Sept. 17, 1971, abandoned, and a continuation-in-part of Ser. No. 256,253, May 24, 1972, abandoned.

[52] U.S. Cl. .......................... 424/251; 260/251 A; 260/240 K; 260/256.4 F
[51] Int. Cl.² ............................ A61K 31/505
[58] Field of Search ............... 260/251 A, 256.4 F, 260/240 K; 424/251

[56] References Cited

UNITED STATES PATENTS

| | | | |
|---|---|---|---|
| 3,149,112 | 9/1964 | Allen | 260/256.4 |
| 3,563,981 | 2/1971 | Lesher | 260/240.3 |
| 3,585,198 | 6/1971 | Meszaros et al. | 260/251 A |
| 3,642,797 | 2/1972 | Lesher | 260/251 A |

OTHER PUBLICATIONS

Antaki et al., J. Chem. Soc., pp. 551–555 (1951).

*Primary Examiner*—Donald G. Daus
*Assistant Examiner*—D. G. Rivers
*Attorney, Agent, or Firm*—Lawrence S. Levinson; Merle J. Smith; Burton Rodney

[57] ABSTRACT

Compounds of the formula

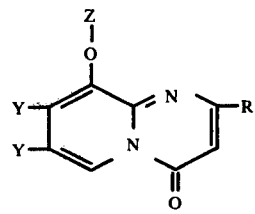

wherein
 R may be hydrogen or a straight or branched chain alkyl radical of from 1 to 10 carbon atoms, aryl of from 6 to 10 carbon atoms, or aralkyl of from 7 to 10 carbon atoms;
 Y may be hydrogen, alkyl of from 1 to 4 carbons, $CF_3$, F, Cl, or Br; and
 Z may be hydrogen or as defined hereinafter.

These compounds are useful as central nervous system stimulants or more specifically in enhancing performance or as mood elevators.

19 Claims, No Drawings

CNS ACTIVE COMPOUNDS

RELATED APPLICATIONS

This application is a continuation-in-part of application Ser. No. 448,133 filed Mar. 4, 1974, now abandoned, which in turn is a continuation-in-part application of Ser. No. 181,565 filed Sept. 17, 1971, now abandoned, and of application Ser. No. 256,253 filed May 24, 1972 now abandoned.

BACKGROUND OF THE INVENTION

Many compounds increase central nervous system (CNS) activity following parenteral administration but are not active or exhibit diminished activity when administered orally. There is a need, therefore, for compounds showing substantial CNS activity following oral administration.

OBJECTS OF THE INVENTION

It is an object of the invention to provide compounds which have CNS activity. Another object is to provide compounds which exhibit CNS activity following oral administration. A further object is to provide a method for the preparation of these compounds. Still another object is to provide pharmaceutical preparations containing as active ingredient the CNS active compounds of the present invention. These and other objects of the present invention will be apparent from the following description.

SUMMARY OF THE INVENTION

Compounds of the formula

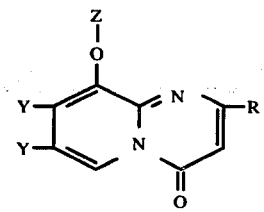

are provided wherein

R may be hydrogen or a straight or branched chain alkyl radical of from 1 to 10 carbon atoms, aryl of from 6 to 10 carbon atoms, or aralkyl of from 7 to 10 carbon atoms;

Y may be hydrogen, alkyl of from 1 to 4 carbons, $CF_3$, F, Cl, or Br; and

Z may be
1. a straight or branched chain alkyl radical of up to 10 carbon atoms; or hydrogen;
2. a substituted straight or branched chain alkyl radical of up to 10 carbon atoms which alkyl radical is substituted by phenyl or a substituted phenyl radical wherein the phenyl substituent is halogen, $CO_2CH_3$, CN, NC, $CF_3$, alkyl of 1 to 4 carbon atoms, alkoxy of 1 to 4 carbon atoms, alkylthio of 1 to 4 carbon atoms or dialkylsulfonamide wherein the dialkyl radicals have a total of 6 carbons;
3. a mono- or di-unsaturated straight or branched chain hydrocarbon radical of from 3 to 10 carbon atoms wherein the carbon atom attached to the oxygen atom is saturated;
4. a substituted mono- or di-unsaturated straight or branched hydrocarbon radical of from 3 to 10 carbon atoms wherein the carbon atom attached to the oxygen atom is saturated and which hydrocarbon radical is substituted by phenyl or a substituted phenyl radical wherein the phenyl substituent is as set forth previously, or by a halogen atom on a carbon atom carrying a double bond, and the acid-addition salts and the amine salts of the formula $NH(R')_2$ of the foregoing compounds exhibit CNS stimulation.

DETAILED DESCRIPTION

It has now been found that CNS active compounds may be prepared by reacting 2-amino-3-pyridinol of formula I or a derivative thereof substituted in either the 4- or 5-position, or both, by the substituent Y wherein Y is as previously defined provided each Y may be hydrogen, with a 3-amino-3-R-substituted $\alpha$,$\beta$-unsaturated ester of formula II wherein R is hydrogen, alkyl of from 1 to 10 carbons, aryl of from 6 to 10 carbons, e.g. phenyl, tolyl, xylyl, mesityl, duryl or naphthyl, or aralkyl of from 7 to 10 carbons, e.g. benzyl or phenethyl. The reaction proceeds in two steps. In the first step, at temperatures of from about 110° to about 130° or above, reaction occurs with the formation of an ammonium salt of formula III wherein R is as defined above. Compound III, in the second step, at temperatures of about 130° or above, evolves ammonia to give Compound IV. These two steps occur in the presence or absence of a solvent, preferably in the presence of a solvent. Suitable solvents include toluene, xylene, diethylbenzene, diphenyl ether or a mixture of diphenyl ether and biphenyl, e.g. Dowtherm A, dimethylformamide, or a mixture of two or more of the foregoing solvents. The heating to decompose the ammonium salt may be carried out at about atmospheric pressure or below atmospheric pressure.

The intermediate IV is then reacted with a compound of the formula Cl-Z or Br-Z wherein Z is as previously defined. This reaction takes place in the presence of a base in an aqueous or non-aqueous system. A co-solvent such as a water-miscible or water-soluble alcohol may be employed with the aqueous system. In the aqueous system the base may be a water-soluble or water-insoluble alkali selected from alkali metal hydroxides or alkaline earth metal hydroxides, $NH_3$ or mono-, di- or tri-alkyl substituted ammonia. Examples are LiOH, NaOH, KOH, $Mg(OH)_2$, $Ca(OH)_2$, $Ba(OH)_2$. In the nonaqueous system the solvent may be an alkanol of from 1 to 6 carbons, e.g. ethanol, or a ketone of from 1 to 6 carbons, e.g. methylethylketone, or an acyclic or cyclic hydrocarbon of from 5 to 10 carbons, e.g. pentane, hexane, decane, cyclohexane, cyclodecane, benzene, toluene, xylene, mesitylene, durene, or an aprotic solvent, e.g. dimethylformamide, dimethylsulfoxide or acetonitrile, and the like. The base used with the foregoing solvents may be an alkali or alkaline earth metal hydroxide as mentioned above (except $NH_4OH$) or an alkali or alkaline earth carbonate or bicarbonate, e.g. $(NH_4)_2CO_3$, $Li_2CO_3$, $Na_2CO_3$, $K_2CO_3$, $MgCO_3$, $BaCO_3$, $NaHCO_3$, $KHCO_3$ or an alkali or alkaline earth metal alkoxide of from 1 to 4 carbons, e.g., $LiOCH_3$, $NaOC_2H_5$, $K-t-OC_4H_9$, $Mg(OC_2H_5)_2$, or $Ca(t-OC_4H_9)_2$, or an alkaline phosphate, e.g., $K_2HPO_4$, $Na_2HPO_4$, $NaKHPO_4$, $CaHPO_4$.

The reaction between the compound of formula IV and the halide Cl-Z or Br-Z in the presence of the base in either the aqueous or non-aqueous system takes place at temperatures of from about room temperature to about 100° C in about 2 to about 24 hours to obtain the final product V.

The foregoing reaction sequence is illustrated by the following equations wherein Y, R and Z are as previously defined:

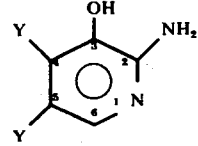

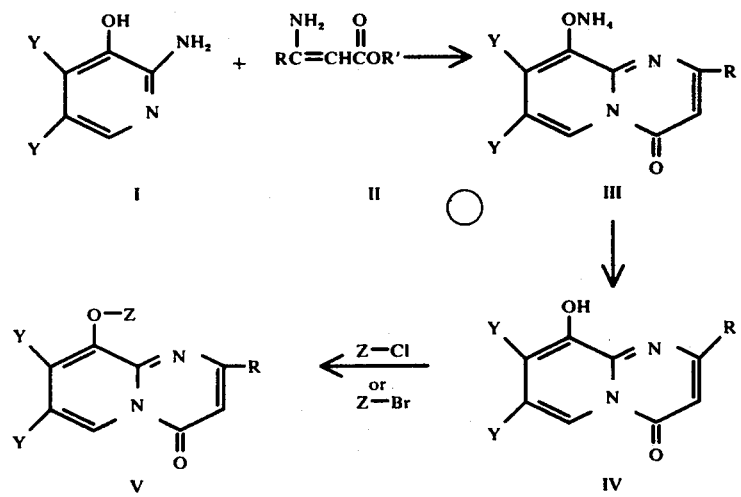

A general method for the preparation of the 3-amino-3-R-substituted-α,β-unsaturated ester is to react with ammonia an acetoacetic ester of the formula

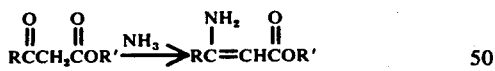

wherein R is as defined previously and R' is an organic radical such as alkyl of from 1 to 12 carbons and preferably 1 to 3 carbons, cycloalkyl of from 3 to 6 carbons, or arylalkyl of from 7 to 10 carbons such as benzyl or phenethyl. The reaction takes place by cooling the ester, e.g., to about 10° C, and bubbling ammonia through the reaction vessel.

The 2-amino-3-pyridinol may be substituted in either the 4- or 5-position, or both, by the substituent Y wherein Y is halogen, alkyl of 1 to 4 carbons or trifluoromethyl. However, it will be appreciated that where both Y's are other than hydrogen, only one of the Y's will be a bulky group such as t-butyl or trifluoromethyl. Examples of some specific substituted 2-amino-3-pyridinols are those corresponding to the compound of formula I wherein the substituent Y in the 4- or 5-position is indicated in the following columns:

| 4-position | 5-position |
|---|---|
| F | H |
| H | F |
| F | F |
| Cl | H |
| H | Cl |
| Cl | Cl |
| Br | H |
| H | Br |
| Br | Br |
| Cl | F |
| F | Cl |
| Br | F |
| F | Br |
| Br | Cl |
| Cl | Br |
| CH$_3$ | H |
| H | CH$_3$ |
| CH$_3$ | CH$_3$ |
| F | CH$_3$ |
| CH$_3$ | F |
| Cl | CH$_3$ |
| CH$_3$ | Cl |
| Br | CH$_3$ |
| CH$_3$ | Br |
| F | CF$_3$ |
| CH$_3$ | CH$_2$CH$_3$ |
| CH$_3$ | CH$_2$CH$_2$CH$_3$ |
| Cl | —CH$_2$CHCH$_3$<br>\|<br>CH$_3$ |
| CH$_2$CH$_2$CH$_2$CH$_3$ | F |
| (CH$_3$)$_3$C | Cl |
| CH$_2$CHCH$_3$<br>\|<br>CH$_3$ | Br |

The 4-, 5-, or 4,5- Y-substituted 2-amino-3-pyridinols may be prepared according to the following reaction sequences, all temperatures being expressed in degrees Centigrade:

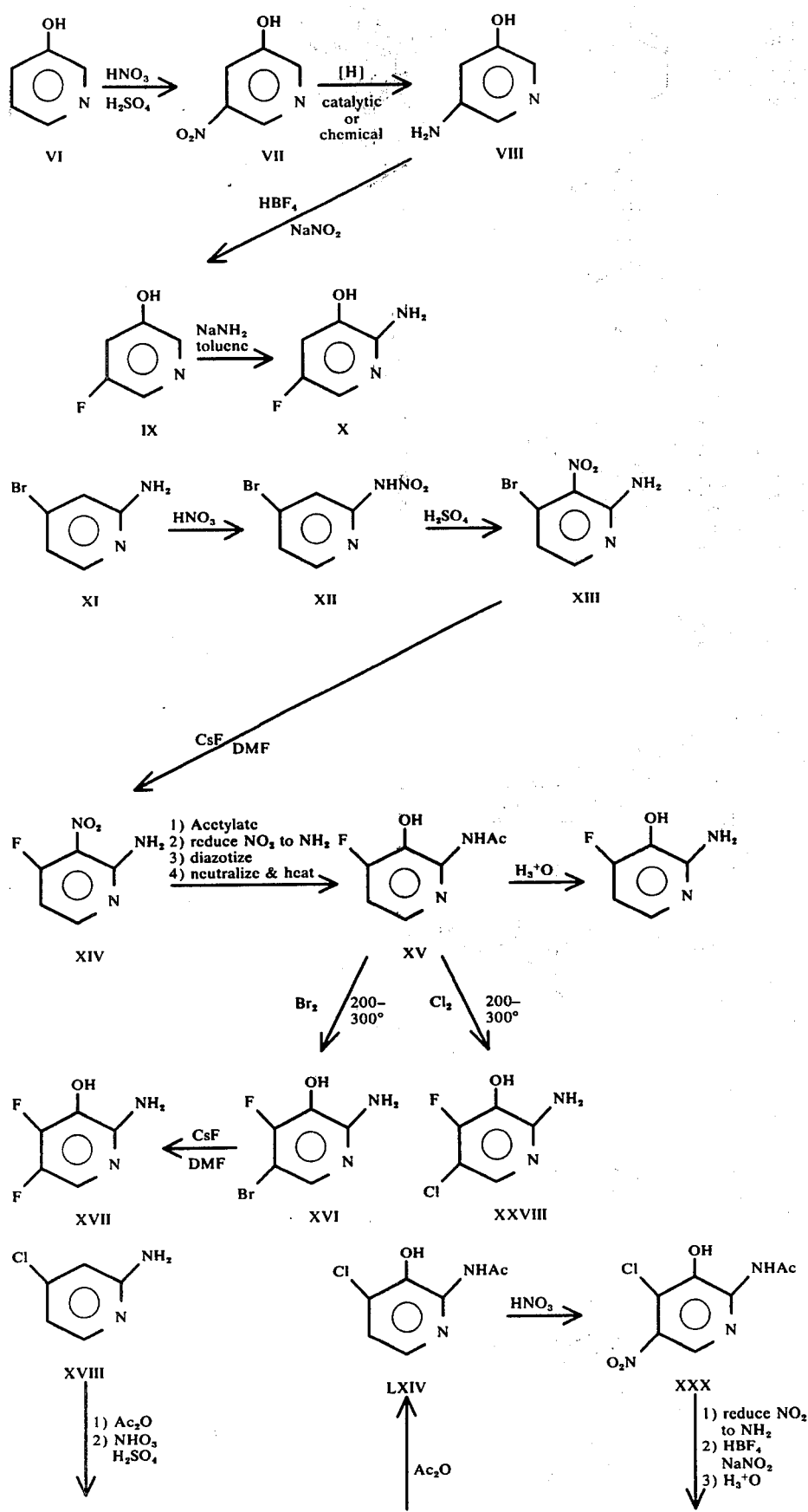

-continued
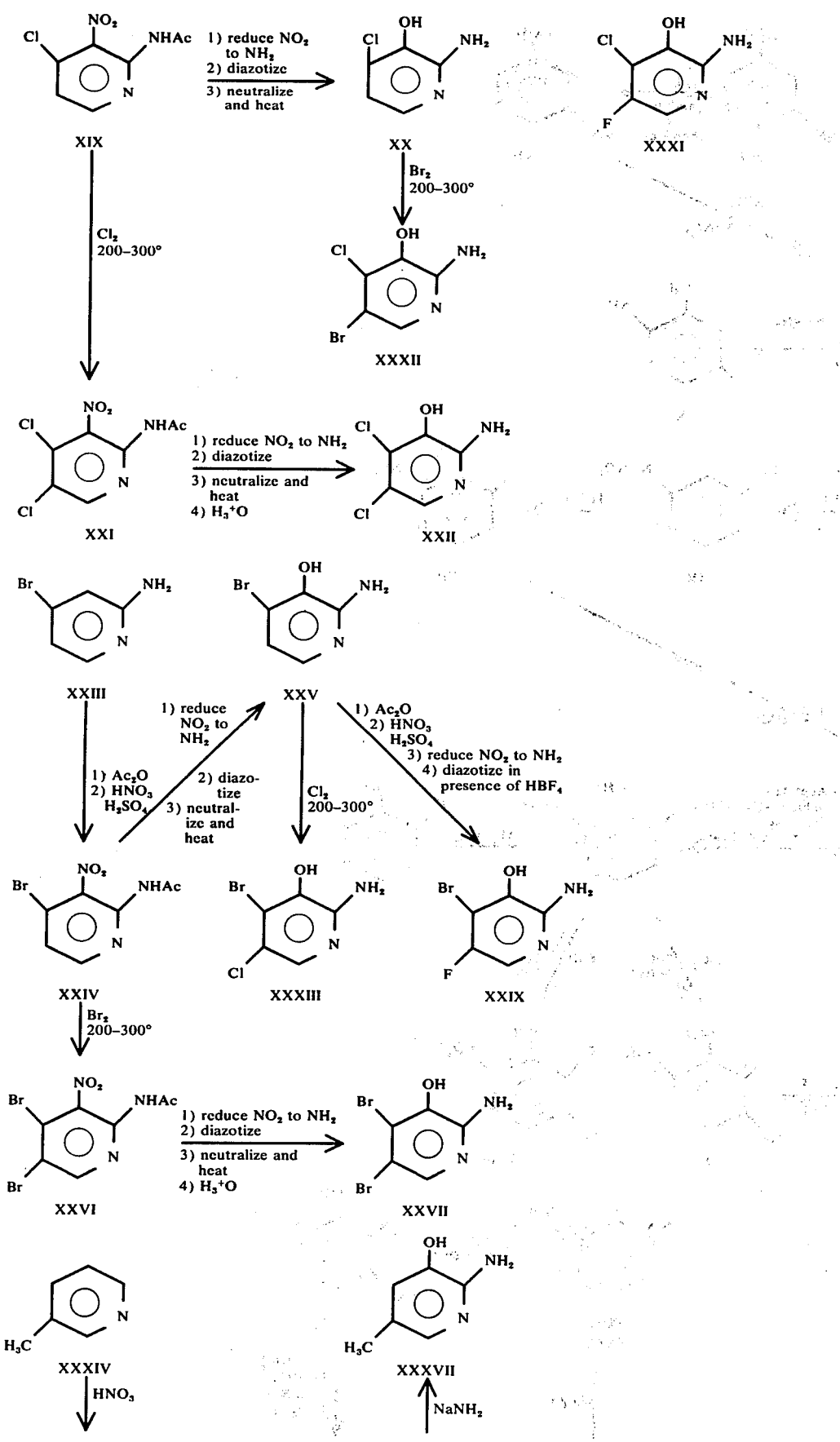

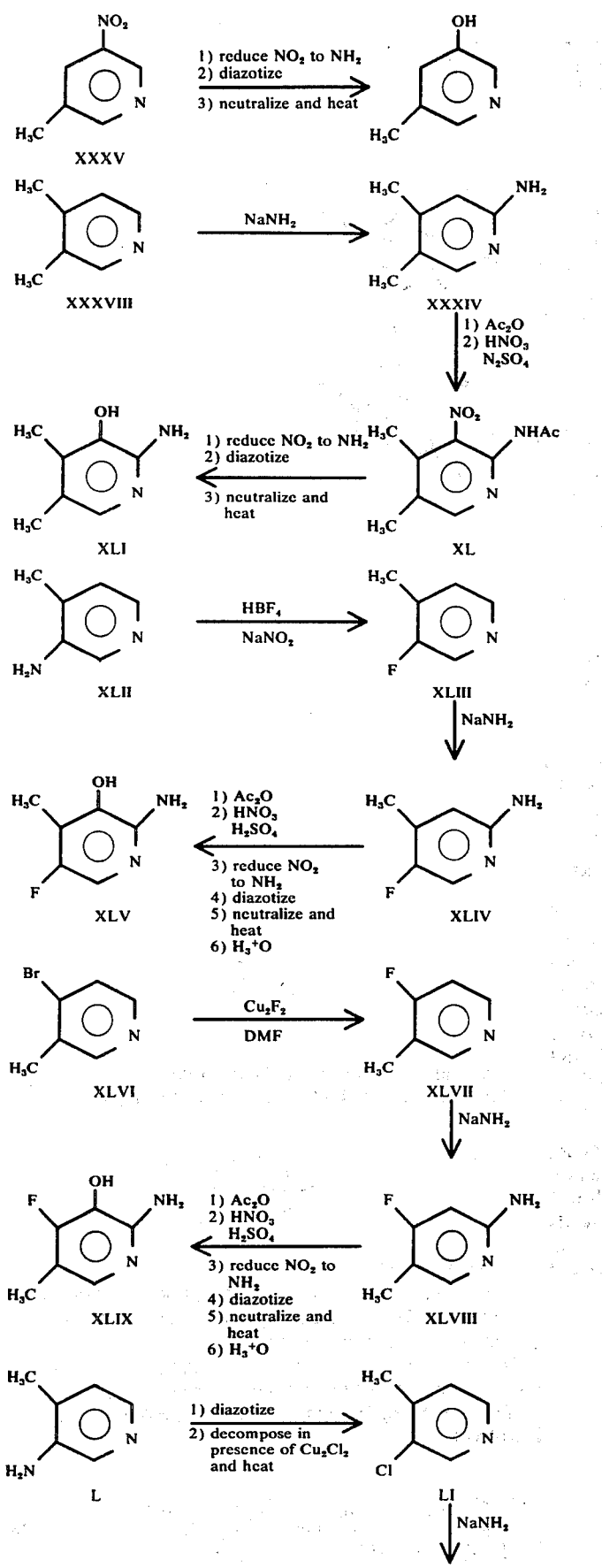

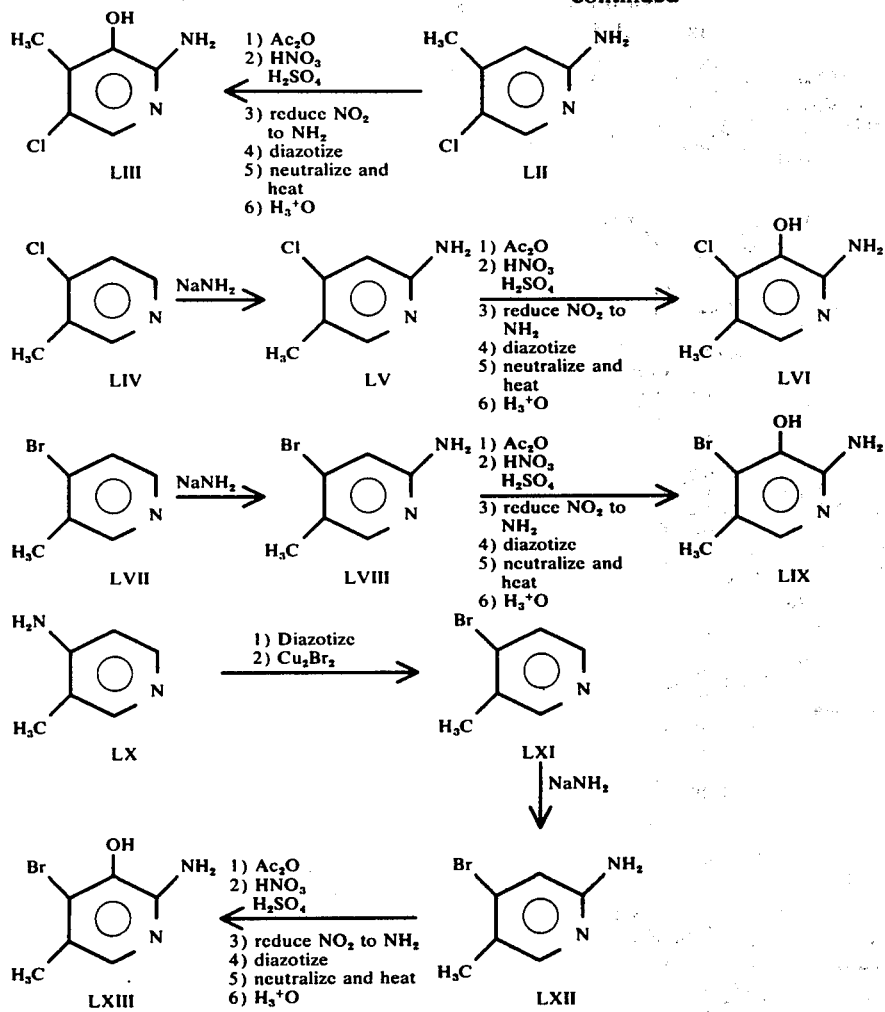

The compounds of the present invention may be used per se or in the form of their non-toxic pharmaceutically acceptable acid-addition salts. Particular acids useful for preparing these acid-addition salts include, inter alia, inorganic acids, such as the hydrohalic acids, preferably hydrochloric and hydrobromic acid, sulfuric acid, nitric acid, boric acid and phosphoric acid, and organic acids such as oxalic, tartaric, fumaric, maleic, citric, acetic, succinic, or, theophylline and 8-chlorotheophylline.

Compounds of formula IV are amphoteric and can, therefore, form salts with organic bases, i.e., primary and secondary amines, via the strongly acid hydroxyl group at position -9, or with mineral and organic acids via the basic nitrogen atom at position -1. Thus, also included among the CNS stimulatory compounds of the invention are the amine salts of the formula

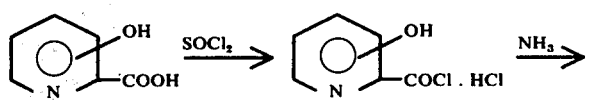

wherein $R_1$ and $R_2$ are H, alkyl of 1–4 carbons, or

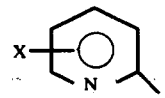

wherein X is H or OH, provided only one of $R_1$ and $R_2$ is H and provided when one of $R_1$ and $R_2$ is

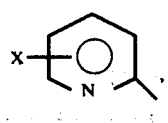

the other is H.

The amine salts and the acid-addition salts provide a more rapid onset of activity compared to the base compounds of the present invention.

The 2-aminopyridinols are prepared by subjecting the desired hydroxy-substituted picolinic acid to the Hofmann degradation reaction. The reaction sequence is as follows:

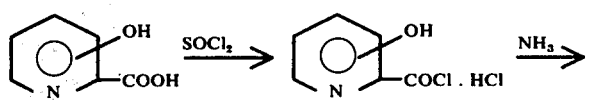

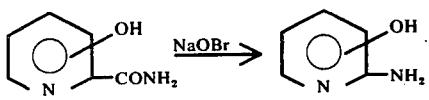

The compounds of this invention are therapeutically active compounds which are utilizable as central nervous system stimulants. More specifically, they are performance enhancers and mood elevators. For these purposes, they may be administered orally or parenterally in such form as tablets, capsules, injectables, or the like by incorporating the appropriate dosage of the compound with carriers according to accepted pharmaceutical practices.

The dose for mammals would be initially about 8–12 mg/kg per day, administered in divided doses. This level would be maintained for 4 to 6 days, and would then be increased to about 16–24 mg/kg per day in divided doses for complete therapeutic maintenance.

The new compounds of Formula V are also useful as antimicrobial agents and may be used to combat infections in animal species, such as mice, rats, dogs, guinea pigs, and the like, due to organisms such as *Trichomonas vaginalis, Trichomonas foetus, Staphyloccocus aureus, Salmonella schottmuelleri, Klebsiella pneumoniae, Proteus vulgaris, Escherichia coli, C. albicans,* or *Trichophyton mentagrophytes*. For example, a compound or mixture of compounds of Formula V may be administered orally to an infected animal, e.g. to a mouse, in an amount of about 5 to 25 mg. per kg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. They may also be applied topically, e.g., to dermatophytosis in a guinea pig, in a lotion, salve or a cream at a concentration of about 0.01 to 3 percent by weight.

They may also be used as surface disinfectants. About 0.01 to 1 percent by weight of any of these substances may be dispersed on an inert solid or in a liquid such as water and applied as a dust or spray. They may be incorporated also, for example, in a soap or other cleansing agent, e.g. a solid or liquid detergent, detergent composition, for example, in general cleaning, in cleaning dairy barns or equipment or cleaning food handling or processing equipment.

All temperatures in the present application are expressed in degrees Centigrade. The following examples illustrate the invention without, however, limiting the same thereto.

EXAMPLE I-1

2-Amino-5-fluoro-3-pyridinol

The diazotization of 5-amino-3-pyridinol in fluoboric acid [according to the procedure of Roe et al., J. Am. Chem. Soc., 69, 2443 (1947)] gives 5-fluoro-3-pyridinol. Reaction of the latter with sodium amide at a temperature of 165° gives 2-amino-5-fluoro-3-pyridinol.

EXAMPLE I-2

2-Amino-4-fluoro-3-pyridinol

4-Bromo-2-nitraminopyridine, 21.5g. in 50 ml of concentrated sulfuric acid is warmed slowly to 40° and kept at 40 for 1 hour to give 2-amino-4-bromo-3-nitropyridine. The latter, 10.8g., 7.5 g. of cesium fluoride, and 100 ml. of dimethylformamide are heated under reflux (155°) for 6 hours and then concentrated to dryness in vacuo. The residue is washed with water and recrystallized from hexane to give 2-amino-4-fluoro-3-nitropyridine. Subsequently, this intermediate is heated under reflux with three volumes of acetic anhydride to give 2-acetamido-4-fluoro-3-nitropyridine. This last derivative is catalytically hydrogenated to give 2-acetamido-3-amino-4-fluoropyridine, and this is diazotized and the diazonium compound decomposed and hydrolyzed by known procedures to yield 2-amino-4-fluoro-3-pyridinol.

EXAMPLE I-3

2-Amino-5-bromo-4-fluoro-3-pyridinol and 2-Amino-4,5-difluoro-3-pyridinol

The 2-amino-4-fluoro-3-pyridinol from Example 2 and bromine in a molar ratio of 1:1 are heated in the vapor phase at 300° according to the procedure of McElvain and Goese [J. Am. Chem. Soc., 65, 2227 (1943)] to give 2-amino-5-bromo-4-fluoro-3-pyridinol. The latter with an equivalent amount of cesium fluoride by the procedure of Example 2, gives 2-amino-4,5-difluoro-3-pyridinol.

EXAMPLE I-4

2-Amino-4-(trifluoromethyl)-3-pyridinol

When 4-(trichloromethyl)pyridine and antimony trifluoride in a molar ratio of 1:1 are heated at 125° for 6 hours and then distilled, there is obtained 4-(trifluoromethyl)pyridine. When the latter is treated with sodium amide as in Example I-1, the product isolated is 2-amino-4-(trifluoromethyl)pyridine. Employing the procedure of Example I-2, this is then converted to 2-amino-3-nitro-4-(trifluoromethyl)pyridine, and in turn as shown in Example I-2, to 2-amino-4-(trifluoromethyl)-3-pyridinol.

EXAMPLE I-5

2-Amino-4-chloro-3-pyridinol

The reaction of 4-chloro-2-nitraminopyridine with concentrated sulfuric acid at 40° gives, according to Example I-2, 2-amino-4-chloro-3-nitropyridine. The procedure of Example I-2 is then followed with this intermediate to give 2-amino-4-chloro-3-pyridinol.

Example I-6

2-Amino-4,5-dichloro-3-pyridinol

When 10.0 g. of 4-chloro-2-amino-3-nitropyridine, from Example I-5, and 20 ml of acetic anhydride are heated under reflux for 1 hour and then concentrated, there is obtained 2-acetamido-4-chloro-3-nitropyridine, and, this, heated at 300° C and treated with chlorine gives 2-acetamido-4,5-dichloro-3-nitropyridine. The latter by the procedure of Example I-2 gives 2-amino-4,5-dichloro-3-pyridinol.

EXAMPLE I-7

2-Amino-4-bromo-3-pyridinol

By substituting 4-bromo-2-nitraminopyridine for the 4-chloro-2-nitraminopyridine in Example I-5, there is obtained 2-amino-4-bromo-3-pyridinol.

EXAMPLE I-8

2-Amino-4,5-dibromo-3-pyridinol

The addition of 4-bromo-2-nitraminopyridine to concentrated sulfuric acid at 40°, portionwise, results in the rearrangement to give 2-amino-4-bromo-3-nitropyridine. Employing the procedure of Example I-6, this is converted to the 2-acetamido derivative and then, with bromine, at 300° to give 2-acetamido-4,5-dibromo-3-nitropyridine. The latter by the procedure of Example I-2 gives 2-amino-4,5-dibromo-3-pyridinol.

EXAMPLE I-9

2-Amino-5-chloro-4-fluoro-3-pyridinol

When chlorine is substituted for the bromine in Example I-3, there is obtained 2-amino-5-chloro-4-fluoro-3-pyridinol.

EXAMPLE I-10

2-Amino-5-bromo-4-fluoro-3-pyridinol

When 2-amino-4-fluoro-3-pyridinol and bromine in a 1:1 molar ratio are passed through a glass tube heated at 350°, and the exit gases condensed and distilled, there is obtained 2-amino-5-bromo-4-fluoro-3-pyridinol.

EXAMPLE I-11

2-Amino-5-chloro-4-fluoro-3-pyridinol

By substituting an equivalent amount of chlorine for the bromine in Example I-10, there is obtained 2-amino-5-chloro-4-fluoro-3-pyridinol.

EXAMPLE I-12

2-Amino-5-bromo-4-chloro-3-pyridinol

By allowing a melt of 2-amino-4-chloro-3-pyridinol to pass down a vertical tube heated at 325° while a stream of bromine gas is forced to pass upward through the tube, the effluent from the reactor tube is shown to contain 2-amino-5-bromo-4-chloro-3pyridinol.

EXAMPLE I-13

2-Amino-4-bromo-5-chloro-3-pyridinol

The procedure of Example I-12 is followed with 2-amino-4-bromo-3-pyridinol and chlorine to give 2-amino-4-bromo-5-chloro-3-pyridinol.

EXAMPLE I-14

5-Methyl-2-amino-3-pyridinol

Following the procedure of Example I-1 and employing sodium amide with 5-methyl-3-pyridinol, there is obtained a mixture of 2-amino-5-methyl-3-pyridinol and 6-amino-5-methyl-3-pyridinol. From this mixture is separated the desired 5-methyl-2-amino-3-pyridinol.

EXAMPLE I-15

2-Amino-4,5-dimethyl-3-pyridinol

The procedure of Example I-1 with 3,4-dimethylpyridine and sodium amide gives 2-amino-4,5-dimethylpyridine. When the latter is subjected to the procedure first of forming the 2-nitramino derivative and then following the procedure of Example I-2, there is obtained 2-amino-4,5-dimethyl-3-pyridinol.

EXAMPLE I-16

2-Amino-5-fluoro-4-methyl-3-pyridinol

When 3-amino-4-picoline is subjected to diazotization in fluoboric acid as in Example I-1, there is obtained 3-fluoro-4-picoline. Treatment of the latter intermediate with sodium amide as in Example I-1, gives 2-amino-5-fluoro-4-picoline. Following the procedure of Example I-15, but substituting 2-nitramino-5-fluoro-4-picoline, there is obtained 2-amino-5-fluoro-4-methyl-3-pyridinol.

EXAMPLE I-17

2-Amino-4-fluoro-5-methyl-3-pyridinol

When 4-bromo-3-picoline and cuprous fluoride in a 1:5 molar ratio is heated in dimethylformamide at 155° for 6 hours there is obtained 4-fluoro-3-picoline. The procedure of Example I-16 is then followed, beginning with the reaction with sodium amide to give first 2-amino-4-fluoro-5-picoline and finally, via Example I-15, 2-amino-4-fluoro-5-methyl-3-pyridinol.

EXAMPLE I-18

2-Amino-5-chloro-4-methyl-3-pyridinol

When 3-amino-4-picoline is diazotized in hydrochloric acid solution and the diazonium compound decomposed in the presence of cuprous chloride there is obtained 3-chloro-4-picoline. By employing this intermediate in the procedure of Example I-16, there is obtained 2-amino-5-chloro-4-methyl-3-pyridinol.

EXAMPLE I-19

2-Amino-4-chloro-5-methyl-3-pyridinol

Starting with 4-chloro-3-picoline and following the procedure of Example I-15, there is obtained 2-amino-4-chloro-5-methyl-3-pyridinol.

EXAMPLE I-20

2-Amino-5-bromo-4-methyl-3-pyridinol

Subjecting 2-amino-4-picoline to the procedure of Example I-15, there is obtained 2-amino-5-bromo-4-methyl-3-pyridinol.

EXAMPLE I-21

2-Amino-4bromo-5-methyl-3-pyridinol

By replacing the 4-chloro-3-picoline with an equivalent amount of 4-bromo-3-picoline and then following the procedure of Example I-19, there is obtained 2-amino-4-bromo-5-methyl-3-pyridinol.

EXAMPLE I-22

2-Amino-5-fluoro-4-(trifluoromethyl)-3-pyridinol

Treatment of 4-methyl-3-pyridinol with a mixture of $PBr_5$ and $POBr_3$ according to the procedure of Fischer [Ber., 32, 1297 (1899)] gives 3-bromo-4-picoline. Chlorination of this intermediate according to the procedure of McBee [Ind. Eng. Chem., 39, 389 (1947)] gives 3-bromo-4-(trichloromethyl) pyridine. The latter, by the procedure described in Examples I-3 and I-4 gives 2-amino-5-fluoro-4-(trifluoromethyl)-3-pyridinol.

EXAMPLE I-23

Preparation of 2-amino-4-pyridinol

*a.* 4-Hydroxypicolinoyl chloride hydrochloride

A mixture of 139.0 g of 4-hydroxypicolinic acid and 238.0 g of thionyl chloride are heated in an oil bath at 70° until solution occurs. The mixture is concentrated in vacuo to remove the excess thionyl chloride and to leave a residue of 4-hydroxypicolinoyl chloride hydrochloride as a colorless solid.

*b.* 4-Hydroxypicolinamide

To 200 ml of concentrated aqueous ammonia (d 0.90) at room temperature, with stirring, is added portionwise, the finely powdered product from (a). When the addition is complete, the mixture is warmed to 70° by means of a steam bath and kept at that temperature for 1 hour. Subsequently, the mixture is concentrated to dryness in vacuo and the solid residue extracted repeatedly with four 200 ml portions of absolute ethanol. The combined extracts are concentrated to 600 ml, filtered hot, and the filtrate concentrated to 200 ml. On cooling, crystals of 4-hydroxypicolinamide separate. When the cooling is completed, the solid is filtered to give 4-hydroxypicolinamide.

*c.* 2-Amino-4-pyridinol

To a solution of 16.0 g of bromine in 280 ml of 10% aqueous potassium hydroxide at 20° is added, portionwise, 13.8 g of finely powdered 4-hydroxypicolinamide. The mixture is stirred during the addition and after the addition is complete until a clear solution forms. Subsequently, the internal temperature is gradually raised to 80°, kept at 80° for 0.25 hour, and the solution is allowed to cool spontaneously to 20°, and is then cooled to 0° by means of an ice bath. The cold solution is treated with glacial acetic acid until the pH is adjusted to 5.5. The precipitate that forms is filtered to give 2-amino-4-pyridinol as a colorless, microcrystalline powder.

EXAMPLE I-24

Preparation of 2-amino-5-pyridinol

By substituting 139.0 g of 5-hydroxypicolinic acid for the 4-hydroxypicolinic acid in example 1 (a), (b) and (c), there is obtained 2-amino-5-pyridinol, as a colorless, granular solid.

EXAMPLE I-25

Preparation of 2-amino-3-pyridinol

By substituting 139.0 g of 3-hydroxypicolinic acid for the 4-hydroxypicolinic acid in example 1(a), (b) and (c), there is obtained 2-amino-3-pyridinol, as a colorless granular solid.

EXAMPLE 1

9-Hydroxy-2-methyl-4H-pyrido[1,2-a]pyrimidin-4one

A mixture of 110.0 g of 2-amino-3-pyridinol and 130.0 g of methyl 2-aminocrotonate are heated at an internal temperature of 110°–115° for approximately 4 hours. The solid product is sublimed in vacuo to give about 140.0 g of product, m.p. 144°–145°.

EXAMPLE 2

7-Bromo-9-hydroxy-2-methyl-4H-pyrido[1,2-a]pyrimidin-4-one

A. When a mixture of 189.0 g of 2-amino-5-bromo-2-pyridinol and 130.0 g of methyl 2-aminocrotonate is heated for 4 hours at an internal temperature of about 150°, a solid reaction product is formed. This solid is suspended in 2 liters of chloroform and 240 ml of water, and 20% aqueous acetic acid is added to adjust the aqueous phase to pH 5.5 The chloroform solution is separated, washed with saturated aqueous sodium chloride, dried, and concentrated to give 180.5 g of 7-bromo-9-hydroxy-2-methyl-4H-pyrido[1,2-a]pyrimidin-4-one.

B. The 2-amino-5-bromo-3-pyridinol is prepared by dissolving 110.0 g of 2-amino-3-pyridinol in 250 ml of 95% ethanol. The solution is cooled to about 5° C and at that temperature is treated with 160 g of liquid bromine during 2 hours. The mixture is stirred for 1 hour after the addition is completed and then concentrated to give 170.6 g of 2-amino-5-bromo-3-pyridinol.

EXAMPLE 3

7-Chloro-9-hydroxy-2-methyl-4H-pyrido[1,2-a]pyrimidin-4one

A. Into a solution of 110.0 g of 2-amino-3-pyridinol in 250 ml of 10% aqueous sulfuric acid at 20° is bubbled a stream of chlorine gas so adjusted that only a few bubbles escape. The addition of 75.0 g of chlorine requires 2 hours. The mixture is cooled to 0° C, the pH adjusted to 5.5, and the whole extracted thoroughly with chloroform. The chloroform solution is washed with saturated aqueous sodium chloride, dried, and concentrated to give 125.4 g of 2-amino-5-chloro-3-pyridinol.

B. By substituting 144.5 g of the product from A for the 2-amino-5-bromo-3-pyridinol in Example 2A, there is obtained 7-chloro-9-hydroxy-2-methyl-4H-pyrido[1,2-a]-pyrimidin-4-one.

EXAMPLE 4

9-Hydroxy-2,8-dimethyl-4H-pyrido[1,2-a]pyrimidin-4-one, hydrochloride

A. A mixture of 218.0 g of 4-methyl-3-pyridinol and 78.0 g of sodium amide are placed in a pressure vessel and heated at 150° for 6 hours. The vessel is allowed to cool, the solid mass is removed and added portionwise to 1 l. of cold 2-propanol. Subsequently, 20% aqueous acetic acid is added until the pH is 5.5 and the whole concentrated to dryness in vacuo. The residue is extracted thoroughly with chloroform and the chloroform extracts washed with saturated aqueous sodium chloride, dried and concentrated. The residue is fractionally crystallized from ethyl acetate to give 2-amino-4-methyl-3-pyridinol.

B. By substituting 125.0 g of the product from A for the 2-amino-5-bromo-3-pyridinol in Example 2A, there is obtained 9-hydroxy-2,8-dimethyl-4H-pyrido[1,2-a]pyrimidin-4-one.

C. Into a solution of 19.0 g of the product from B in 200 ml of dry chloroform, at 0°, is bubbled dry hydrogen chloride until no further precipitation occurs. The crystalline product is filtered and recrystallized from ethanol to give 9-hydroxy-2,8-dimethyl-4H-pyrido[1,2-a]-pyrimidin-4-one hydrochloride.

EXAMPLE 5

9-[(o-Bromobenzyl)oxy]-2-methyl-4H-pyrido[1,2-a]pyrimidin-4-one

To 35.2 g of 9-hydroxy-2-methyl-4H-pyrido[1,2-a]pyrimidin-4-one suspended in 100 ml of absolute ethanol is added a solution of 11.0 g of sodium methoxide in 165 ml of absolute ethanol. To this is then added 50.0 g o-bromobenzyl bromide dissolved in 25 ml of absolute ethanol. The mixture is then heated under reflux for about 6 hours and worked up to give 9-[(o-bromobenzyl)oxy]-2-methyl-4H-pyrido[1,2-a]-pyrimidin-4-one, m.p. 144°–146°, after recrystallization from ethyl acetate.

EXAMPLE 6

9-[(Allyl)oxy]-2-methyl-4H-pyrido[1,2-a]pyrimidin-4-one

To 3.52 g of 9-hydroxy-2-methyl-4H-pyrido[1,2-a]-pyrimidin-4-one in 100 ml of pure ethyl methyl ketone is added 3.31 g of micronized anhydrous potassium carbonate and 2.90 g of allyl bromide. The mixture is stirred and heated under reflux for about 6 hours and then cooled. To the mixture is added 20 ml of water and the whole stirred vigorously, filtered with suction, the water layer separated, the organic layer washed with saturated aqueous sodium chloride, dried, and concentrated. The residue is recrystallized from heptane to give 9-[(allyl)oxy]-2-methyl-4H-pyrido[1,2-a]-pyrimidin-4-one, m.p. 113°–115°.

EXAMPLE 7

9-[(2,4-Dichlorobenzyl)oxy]-2-methyl-4H-pyrido[1,2-a]-pyrimidin-4-one, Hydrobromide A. To a solution of 6.6 g of potassium hydroxide (85%) and 10.3 g of sodium bromide in 100 ml of water and 150 ml of methanol is added, in portions, 17.6 g of 9-hydroxy-2-methyl-4H-pyrido[1,2-a]pyrimidin-4-one and the mixture stirred for 0.25 hours. To this is then added 19.6 g of 2,4-dichlorobenzyl chloride dissolved in 50 ml of 95% ethanol and the mixture stirred and refluxed for about 6 hours. The mixture is concentrated to dryness in vacuo and the residue is distributed between 500 ml of chloroform and 250 ml of water. Workup of the chloroform solution yields 9-[(2,4-dichlorobenzyl)oxy]-2-methyl-4H-pyrido[1,2-a]-pyrimidin-4-one, m.p. 180°–182° after recrystallization from acetonitrile.

B. The product from A, 3.35 g, is dissolved in 25 ml of dry chloroform and to this added 0.81 g of hydrogen bromide in 5 ml of glacial acetic acid. The mixture is diluted with 25 ml of anhydrous ether, the cyrstalline product is filtered and recrystallized from 2-propanol to give 9-[2,4-dichlorobenzyl)oxy]-2-methyl-4H-pyrido[1,2-a]-pyrimidin-4-one hydrobromide.

EXAMPLE 8

9-[2-Bromo-4-chlorobenzyl)oxy]-2-methyl-4H-pyrido[1,2-a]-pyrimidin-4-one

By substituting 28.6 g of 2-bromo-4-chlorobenzyl bromide for the 19.6 g of 2,4-dichlorobenzyl chloride in Example 6A, there is obtained 9-[(2-bromo-4-chlorobenzyl)oxy]-2-methyl-4H-pyrido[1,2-a]pyrimidin-4-one, m.p. 182°–184° after recrystallization from acetonitrile.

EXAMPLE 9

7-Bromo-9-[(2-phenethyl)oxy]-2-methyl-4H-pyrido[1,2-a]-pyrimidin-4-one

To 5.5 g of sodium methoxide suspended in 100 ml of N,N-dimethylformamide is added 28.6 g of 7-bromo-9-hydroxy-2-methyl-4H-pyrido [1,2-a]pyrimidin-4-one. The mixture is stirred for about 1 hour and to this is added, dropwise, 19.4 g of 2-phenethyl bromide. The mixture is stirred at room temperature for about 16 hours and then worked up to give 7-bromo-9-[(2-phenethyl)oxy]-2-methyl-4H-pyrido[1,2-a]-pyrimidin-4-one.

EXAMPLE 10

7-Chloro-9-(isobutoxy)-2-methyl-4H-pyrido[1,2-a]pyrimidin-4-one

To a stirred suspension of 1.6 g of powdered sodium hydroxide in 100 ml of pure ethyl methyl ketone is added 21. g of 7-chloro-9-hydroxy-2-methyl-4H-pyrido[1,2-a]pyrimidin-4-one. The mixture is stirred for about 1 hour and 1.5 g of isobutyl bromide dissolved in 10 ml of pure ethyl methyl ketone is added dropwise. Subsequently, 0.2 g of copper bronze is added and the mixture stirred and heated under reflux for 2 hours. The mixture is cooled, diluted with 20 ml of water, filtered, and the organic phase in the filtrate separated, washed with saturated aqueous sodium chloride, dried, and concentrated to give 7-chloro-9-(isobutoxy)-2-methyl-4H-pyrido[1,2-a]pyrimidin-4-one.

EXAMPLE 11

9-[(Cinnamyl)oxy]-2,8-dimethyl-4H-pyrido[1,2-a]pyrimidin-4one

To a solution of 6.6 g of potassium hydroxide (85%) and 0.2 g of potassium iodide in 100 ml of water is added 150 ml of methanol and 19.0 g of 9-hydroxy-2,8-dimethyl-4H-pyrido[1,2-a]-pyrimidin-4-one and the whole stirred for about 1 hour. To this is added 20.1 g of cinnamyl bromide dissolved in 20 ml of methanol. The mixture is stirred at room temperature for about 18 hours and then worked up to give 9-[(cinnamyl)oxy]-2,8-dimethyl-4H-pyrido[1,2-a]pyrimidin-4-one.

EXAMPLE 12

2-Methyl-9-[[(m-trifluoromethyl)benzyl]oxy]-4H-pyrido[1,2-a]-pyrimidin-4-one By substituting 19.9 g of (m-trifluoromethyl)benzyl chloride for the 2,4-dichlorobenzyl chloride in Example 7, there is obtained 2-methyl-9-[[(m-trifluoromethyl)benzyl]-oxy]-4H-pyrido[1,2-a]pyrimidin-4-one, m.p. 159°–161°.

EXAMPLE 13

9-[(o-Cyanobenzyl)oxy]-2-methyl-4H-pyrido[1,2-a]pyrimidin-4-one

By following the procedure of Example 5, but substituting 21.6 g of o-cyanobenzyl bromide for the o-bromobenzyl bromide, there is obtained 9-[(o-cyanobenzyl)oxy]-2-methyl-4H-pyrido-[1,2-a]pyrimidin-4-one.

EXAMPLE 14

9-[(p-Methoxybenzyl)oxy]-2-methyl-4H-pyrido[1,2-a]pyrimidin-4-one

A. By following the procedure of Example 5, but substituting 17.2 g of p-methoxybenzyl chloride for the o-bromobenzyl bromide, there is obtained 9-[(p-methoxybenzyl)-oxy]-2-methyl-4H-pyrido[1,2-a]pyrimidin-4-one.

B. To 138.0 g of p-methoxybenzyl alcohol in 500 ml of dry chloroform is added, dropwise, 119 g of thionyl chloride. Subsequently, the mixture is stirred and heated under reflux for 2 hours, concentrated from the steam bath and the residue fractionated to give p-methoxybenzyl chloride.

EXAMPLE 15

2-Methyl-9-[[p-(N,N-dimethylsulfamoyl)cinnamyl]oxy]-4H-pyrido[1,2-a]pyrimidin-4-one A. To 72.0 g of sodium borohydride in 1.5 l. of methanol, with ice cooling, is added 16.30 g of p-amino-cinnamic acid in 500 ml of methanol, maintaining the temperature between 10°–15° C. Subsequent to the addition, the mixture is stirred for 4 hours at room temperature and then worked up to give p-aminocinnamyl alcohol.

B. To 149.0 g of the product from A in 500 ml of 10% aqueous hydrochloric acid, maintained at 0° to 5° C, is added, dropwise, a saturated solution of 69 g of sodium nitrite in water. The mixture is then stirred for 1 hour at the same temperature, and then a rapid stream of sulfur dioxide is passed into the solution for two hours, maintaining the temperature at 0° 5°. The sulfonyl chloride separates from the reaction mixture as an oil; this is extracted in the cold with three successive portions of 100 ml of chloroform. The chloroform extracts are combined, washed with saturated aqueous sodium chloride, and then added dropwise to 250 ml of concentrated aqueous ammonia (d 0.7). The mixture is then heated gradually by means of a steam bath until the chloroform has distilled and the aqueous solution is then cooled to give p-(N,N-dimethylsulfamoyl)cinnamyl alcohol.

C. By following the procedure of Example 13B but substituting 227.0 g of the product from B for the p-methoxybenzyl alcohol, there is obtained p-(N,N-dimethylsulfamoyl)cinnamyl chloride.

D. By the procedure of Example 5, but substituting 28.6 g of the product from C for the o-bromobenzyl bromide, there is obtained 2-methyl-9-[p-(N,N-dimethylsulfamoyl)-cinnamyl]oxy]-4H-pyrido[1,2-a]pyrimidin-4-one.

EXAMPLE 16

9-(3-Chloro-2-butenyloxy)-2-methyl-4H-pyrido[1,2-a]pyrimidin-4-one

By substituting for the o-bromobenzyl bromide in Example 5, 13.8 g of 1,3-dichloro-2-butene, there is obtained 9-(3-chloro-2-butenyloxy)-2methyl-4H-pyrido[1,2-a]pyrimidin-4-one.

EXAMPLE 17

2-Methyl-9-[[p-(methylthio)benzyl]oxy]-4H-pyrido[1,2-a]-4-one

A. By following the procedure of Example 13B, but substituting 154.0 g of (p-methylthio)benzyl alcohol for the p-methoxybenzyl alcohol, there is obtained p-(methylthio)-benzyl chloride.

B. By substituting 19.4 g of the product from A for the o-bromobenzyl bromide in Example 5, there is obtained 2-methyl-9-[[p-(methylthio)benzyl]oxy]-4H-pyrido[1,2-a]-pyrimidin-4-one.

EXAMPLE 18

9-[o-(Carbomethoxybenzyl)oxy]-2-methyl-4H-pyrido[1,2-a]-pyrimidin-4-one

By following the procedure of Example 5, but substituting for the o-bromobenzyl bromide, 20.3 g of o-(carbomethoxy) benzyl chloride, there is obtained 9-[o-(carbomethoxybenzyl)oxy]-2-methyl-4H-pyrido[1,2-a]pyrimidin-4-one, m.p. 175°–177°.

EXAMPLES 19–49

By reacting a 2-amino-3-pyridinol of formula I, wherein the substituent Y in the 4- or 5-position is an indicated in column A, with a 3-amino-3-R-substituted α,β-unsaturated ester of formula II wherein R and R¹ are as indicated in column B, there is obtained the corresponding 9-hydroxy-2-R-substituted-4H-pyrido[1,2-a]pyrimidin-4-one of formula IV wherein the substituents Y and R are as indicated in column A and B respectively.

|         |       | A     |              | B             |
|---------|-------|-------|--------------|---------------|
| Example | $Y_2$ | $Y_1$ | R            | $R^1$         |
|         | F     | H     | H            | $CH_3$        |
|         | H     | F     | $CH_2CH_3$   | $CH_3$        |
|         | Br    | F     | $CH_2CH_3$   | $CH_3$        |
|         | H     | $CF_3$| $CH_2CH_3$   | $CH_3$        |
|         | H     | Cl    | $CH_2CH_2CH_3$ | $CH_3$      |
|         | Cl    | Cl    | $C(CH_3)_3$  | $CH_3$        |
|         | H     | Br    | $CH_2(CH_2)_4CH_3$ | $CH_3$  |
|         | Br    | Br    | $CH_2(CH_2)_6CH_3$ | $CH_3$  |
|         | Cl    | F     | $CH_2(CH_2)_8CH_3$ | $CH_3$  |
| 28      | F     | Br    | $CH(CH_3)_2$ | $CH_3$        |
| 29      | F     | Cl    | $CH(CH_3)_2$ | $CH_2(CH_2)_{10}CH_3$ |

-continued

| | Ia | | II | | IVa | |
|---|---|---|---|---|---|---|
| | Y₁—OH, NH₂ (pyridine) | | NH₂ O; RC=CHCOR' | | Y₁—OH, N=R ring system | |
| | | A | | | B | |
| Example | Y₂ | Y₁ | R | | R¹ | |
| 30 | Br | Cl | CH(CH₃)₂ | | CH₂—phenyl | |
| 31 | Cl | Br | CH(CH₃)₂ | | —cyclohexyl | |
| 32 | CH₃ | H | CH₂C(CH₃)₃ | | CH₃ | |
| 33 | CH₃ | CH₃ | CH₃<br>│<br>CH₂CHCH₂CH₃ | | CH₃ | |
| 34 | F | CH₃ | H | | CH₃ | |
| 35 | CH₃ | F | CH₂CH₃ | | CH₃ | |
| 36 | Cl | CH₃ | H | | CH₃ | |
| 37 | CH₃ | Cl | H | | CH₂CH₃ | |
| 38 | Br | CH₃ | CH₂CH(CH₃)₂ | | CH₂CH₂CH₃ | |
| 39 | CH₃ | Br | CH(CH₃)₂ | | CH₃ | |
| 40 | F | F | CH₂CH₃ | | CH₃ | |
| 41 | H | CH₃ | CH₂CH₂CH₃ | | CH₃ | |
| 42 | F | CF₃ | H | | CH₃ | |
| 43 | H | CF₃ | H | | CH₃ | |
| 44 | CH₃ | CH₂CH₃ | H | | CH₃ | |
| 45 | Br | CH₂CH₂CH₃ | H | | CH₃ | |
| 46 | Cl | CH₂CH(CH₃)₂ | CH₂CH₃ | | CH₃ | |
| 47 | CH₂CH₂CH₂CH₃ | F | CH₂CH₂CH₃ | | CH₃ | |
| 48 | C(CH₃)₃ | Cl | CH(CH₃)₂ | | CH₃ | |
| 49 | CH(CH₃)₂ | Br | CH(CH₃)₂ | | CH₃ | |

EXAMPLES 50–74

By reacting the compound of formula IV prepared as described in the example listed in column A with the halide Z-Cl or Z-Br indicated in column B, there is obtained the corresponding compound of formula V wherein Z is the organic radical of the Z-halide indicated in column B.

| Example | A | B |
|---|---|---|
| | | Z-halide |
| 50 | 2 | o-bromobenzyl-bromide |
| 51 | 3 | allyl bromide |
| 52 | 4 | 2,4-dichlorobenzyl chloride |
| 53 | 2 | 2-bromo-4-chlorobenzyl bromide |
| 54 | 3 | 2-phenethyl bromide |
| 55 | 1 | isobutyl bromide |
| 56 | 1 | cinnamyl bromide |
| 57 | 2 | p-methoxybenzyl chloride |
| 58 | 3 | p-(N,N-dimethylsulfamoyl)-cinnamyl chloride |
| 59 | 3 | 1,3-dichloro-2-butene |
| 60 | 4 | p-(methylthio)benzyl chloride |
| 61 | 2 | o-(carbomethoxy)benzyl chloride |
| 62 | 2 | (m-trifluoromethyl)benzyl chloride |
| 63 | 3 | o-cyanobenzyl bromide |
| 64 | 19 | decyl chloride |
| 65 | 20 | octyl chloride |
| 66 | 21 | 2-ethylhexyl bromide |
| 67 | 22 | benzyl chloride |
| 68 | 23 | p-(carboxymethyl)benzyl chloride |
| 69 | 24 | p-(isocyano)benzyl chloride |
| 70 | 25 | 2,5-heptadienyl chloride |
| 71 | 26 | 2,4-pentadienyl chloride |
| 72 | 27 | 2,3-butadienyl chloride |
| 73 | 28 | 4-chloro-1-butyne |
| 74 | 29 | 4-bromo-1-butene |

EXAMPLES 75–84

Following the procedure of Examples 19–49 but reacting 2-amino-3-pyridinol with a compound of formula II wherein R is as indicated in the column below, and R' is CH₃, there is obtained the corresponding compound of formula IV wherein each Y is hydrogen and R is as indicated in the column below:

| Example | R |
|---|---|
| 75 | —phenyl |
| 76 | —CH₂—phenyl |
| 77 | —phenyl—CH₃ |
| 78 | —phenyl(—CH₃)(CH₃) |
| 79 | —CH₂CH₂—phenyl |
| 80 | —naphthyl |
| 81 | CH₃—phenyl—CH₂Br |
| 82 | phenyl—CH=CCl—CH₂Cl |

-continued

| Example | R |
|---|---|
| 83 | 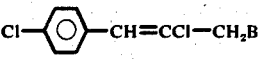 |
| 84 | 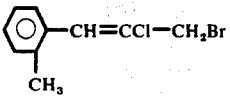 |

EXAMPLES 85–94

By reacting the final product of the example listed in column A with the halide Z-Cl or Z-Br indicated in Column B, there is obtained the corresponding compound of formula V wherein Z is the organic radical of the Z-halide of Column B.

| Example | A | B |
|---|---|---|
| 85 | 75 | o-bromobenzyl bromide |
| 86 | 76 | 2-phenethyl bromide |
| 87 | 77 | benzyl chloride |
| 88 | 78 | cinnamyl bromide |
| 89 | 79 | 4-chloro-1-butene |
| 90 | 80 | 1,3-dichloro-2-butene |
| 91 | 81 | o-bromobenzyl bromide |
| 92 | 82 | 2-phenethyl bromide |
| 93 | 83 | benzyl chloride |
| 94 | 84 | cinnamyl bromide |

EXAMPLE 95

9-(Cinnamyloxy)-2-methyl-4H-pyrido[1,2-a]pyrimidin-4-one

By substituting 15.3 g of cinnamyl chloride for the 2,4-dichlorobenzyl chloride in Example 7, there is obtained about 5.1 g of 9-(cinnamyloxy)-2-methyl-4H-pyrido[1,2-a]-pyrimidin-4-one, m.p. 154°–155°.

EXAMPLE 96

2-Methyl-9-(phenethyloxy)-4H-pyrido1,2-a]pyrimidin-4-one oxalate salt

By substituting 20.5 g of 2-bromoethylbenzene for the 2,4-dichlorobenzyl chloride in Example 7, there is obtained about 17.5 g of the base, 2-methyl-9-(phenethyloxy)-4H-pyrido-[1,2-a]-pyrimidin-4-one, as an oil. The base, 17.5 g in 25 ml of acetonitrile is treated with 5.65 g of oxalic acid in 35 ml of acetonitrile to give about 13.5 g of the oxalate salt, m.p. 191°–193°.

EXAMPLE 97

2-Methyl-9-[[o-(trifluoromethyl)benzyl]oxy]-4H-pyrido[1,2-a]-pyrimidin-4-one

By substituting 19.9 g of (o-trifluoromethyl)benzyl chloride for the (m-trifluoromethyl) benzyl chloride in Example 12 there is obtained about 24.5 g of 2-methyl-9-[[o-(trifluoromethyl)benzyl]oxy]-4H-pyrido[1,2-a]pyrimidin-4-one, m.p. 130°–132°.

EXAMPLE 98

2-Methyl-9-[[p-trifluoromethyl)benzyl]oxy]-4H-pyrido[1,2-a]-pyrimidin-4-one

By substituting 19.9 g of (p-trifluoromethyl) benzyl chloride for the (m-trifluoromethyl) benzyl chloride in Example 12, there is obtained about 36.0 g of the named compound, m.p. 166°–167°.

EXAMPLE 99

9-Butoxy-2-methyl-4H-pyrido[1,2-a]pyrimidin-4-one

By substituting 5.0 g of n-butyl bromide for the allyl bromide in Example 6, there is obtained about 1.5 g of the name compound, m.p. 93°–94°.

EXAMPLE 100

9-[(o-Chlorobenzyl)oxy]-2-methyl-4H-pyrido[1,2-a]pyrimidin-4-one

By substituting 4.9 g of o-chlorobenzyl chloride for the allyl bromide in Example 6, there is obtained about 8.1 g of the named compound, m.p. 166°–168°.

EXAMPLE 101

2-methyl-9-(2-propynyloxy)-4H-pyrido[1,2-a]pyrimidin-4-one

By substituting 2.4 g of propynyl bromide for the allyl bromide in Example 6, there is obtained about 2.5 g of the named compound, m.p. 197°–198°.

EXAMPLE 102

9-(Benzyloxy)-2-methyl-4H-pyrido[1,2-a]pyrimidin-4-one

By substituting 3.8 g of benzyl chloride for the allyl chloride in Example 6, there is obtained about 3.4 g of 9-(benzyloxy)-2-methyl-4H-pyrido[1,2-a]pyrimidin-4-one, m.p. 110°–112°.

EXAMPLE 103

9-Hydroxy-2-methyl-4H-pyrido[1,2-a]pyrimidin-4-one, Diethylamine Salt

To a solution of 1.8 g of 9-hydroxy-2-methyl-4H-pyrido[1,2-a]pyrimidin-4-one in 70 ml of acetonitrile is added 0.7 g of diethylamine. When the mixture is cooled, the salt, m.p. 135°–138°, 2.25 is obtained.

EXAMPLE 104

9-Hydroxy-2-methyl-4H-pyrido[1,2-a]pyrimidin-4-one, 2-amino-6-pyridinol salt

To a solution of 0.88 g of 9-hydroxy-2-methyl-4H-pyrido[1,2-a]pyrimidin-4-one in 40 ml of acetonitrile is added 0.55 g of 2-amino-6-pyridinol in 20 ml of 2-propanol. Cooling the solution that is formed gives 0.62 g of the salt, m.p. 188°–190°.

EXAMPLE 105

9-Hydroxy-2-methyl-4H-pyrido[1,2-a]pyrimidin-4-one, 2-amino-pyridine salt

A solution of 0.88 g of 9-hydroxy-2-methyl-4H-pyrido-[2-a]pyrimidin-4-one in 40 ml of acetonitrile is added 0.47 g of 2-aminopyridine. The solution that is formed is concentrated to a small volume and cooled to give 1.1 g of the salt, m.p. 93°–95°.

EXAMPLE 106

9-Hydroxy-2-methyl-4H-pyrido[1,2-a]pyrimidin-4-one, maleic acid salt

To 1.0 g of 9-hydroxy-2-methyl-4H-pyrido[1,2-a]-pyrimidin-4-one in 10 ml of ethyl methyl ketone is added 0.70 g of maleic acid in 5 ml of ethyl methyl ketone. The salt crystallizes from the cooled solution to give 1.6 g of the salt, m.p. 154°–156°.

EXAMPLE 107

9-Hydroxy-2-methyl-4H-pyrido[1,2-a]pyrimidin-4-one, tartaric acid salt

To 0.88 g of 9-hydroxy-2-methyl-4H-pyrido[1,2-a]-pyrimidin-4-one in 40 ml of acetonitrile is added 0.75 g of tartaric acid in 7 ml of 2-propanol. The salt is obtained by concentration of the solution; it melts at 160 -163°.

EXAMPLE 108

9-Hydroxy-2-methyl-4H-pyrido[1,2-a]pyrimidin-4-one, salt with fumaric acid

To a solution of 0.88 g of 9-hydroxy-2-methyl-4H-pyrido[1,2-a]pyrimidin-4-one in 25 ml of acetonitrile is added 0.58 g of fumaric acid in 10 ml of acetonitrile. The solution that forms is cooled to give 0.85 g of the salt, m.p. 172°-174°.

EXAMPLE 109

9-Hydroxy-2-methyl-4H-pyrido[1,2-a]pyrimidin-4-one, salt with malic acid

To a solution of 0.88 g of 9-hydroxy-2-methyl-4H-pyrido[1,2-a]pyrimidin-4-one in 25 ml of acetonitrile is added 0.67 g of malic acid in 10 ml of acetonitrile. The solution that forms is cooled to give 0.85 g of the salt, m.p. 154°-156°.

EXAMPLE 110

9-Hydroxy-2-methyl-4H-pyrido[1,2-a]pyrimidin-4-one, citric acid salt

Solutions of 0.88 g of 9-hydroxy-2-methyl-4H-pyrido-[1,2-a]pyrimidin-4-one in 40 ml of acetonitrile and 0.96 g of citric acid in 20 ml of 2-propanol are mixed. A clear solution forms and this is concentrated to give the salt as a low-melting solid.

EXAMPLE 111

9-Hydroxy-2-methyl-4H-pyrido[1,2-a]pyrimidin-4-one, n-butylamine salt

A mixture of 0.5 g of 9-hydroxy-2-methyl-4H-pyrido-[1,2-a]pyrimidin-4-one and 7.5 ml of n-butylamine are heated to the b.p., and the solution is then allowed to cool. The salt crystallizes and is filtered to give 0.6 g of salt, m.p. 139°-141°(dec.).

EXAMPLE 112

9-Hydroxy-2-methyl-4H-pyrido[1,2-a]pyrimidin-4-one, 2-amino-3-pyridinol salt

Following the procedure of example 104 but substituting 2-amino-3-pyridinol for the 2-amino-6-pyridonol, the title compound is obtained, m.p. 164°-166° C.

EXAMPLE 113

9-Hydroxy-3-propyl-4H-pyrido[1,2-a]pyrimidin-4-one and its Salt with p-Toluenesulfonic Acid A mixture of 31.5 g of ethyl butyrylacetate, 11.0 g of 2-amino-3-pyridinol, 125 ml of ethyleneglycol monomethyl ether, and 1.0 g of p-toluenesulfonic acid is stirred and heated under reflux for 21 hours and then allowed to cool. The product that crystallizes is filtered and dried to give 10.1 g of 9-hydroxy-2-propyl-4H-pyrido[1,2-a]pyrimidin-4-one, m.p. 95°-96°. The filtrate is concentrated to one-half volume to give 5.8 g of solid, m.p. 92°-94°. This is extracted with two 50 ml portions of boiling diisopropyl ether to leave behind 1.0 g of an insoluble solid. From the diisopropyl ether extracts there is obtained 3.8 g of additional product, m.p. 95°-96°. The 1.0 g of solid insoluble in diisopropyl ether is recrystallized from acetonitrile to give 0.60 g of 9-hydroxy-2-propyl-4H-pyrido[1,2-a]pyrimidin-4-one, salt with p-toluenesulfonic acid, m.p. 202°-204°. The same salt is prepared by mixing rapidly hot solutions of 1.40 g of the product, m.p. 95°-96° in 15 ml of acetonitrile and 1.30 g of p-toluenesulfonic acid in 15 ml of acetonitrile. A clear solution forms briefly and then the salt crystallizes. The yield of salt, m.p. 202°-204°, is 2.16 g.

EXAMPLE 114

9-[(Cinnamyl)oxy]-2-methyl-4H-pyrido[1,2-a]pyrimidin-4-one

By substituting 3.94 g of cinnamyl bromide for the allyl bromide in Example 6, there is obtained 5.6 g of the named compound, m.p. 154°-155°.

What is claimed is:

1. A compound of the formula

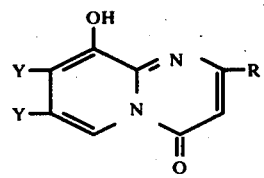

wherein Y is hydrogen, alkyl of from 1 to 4 carbon atoms, $CF_3$, F, Cl or Br provided each Y may be hydrogen and R is a straight or branched chain alkyl radical of from 1 to 10 carbon atoms, and pharmaceutically acceptable acid addition salts thereof and amine salts of the formula $NH(R_1)$ $(R_2)$ wherein $R_1$ and $R_2$ are the same or different and are selected from the group consisting of hydrogen, alkyl of 1-4 carbons, or

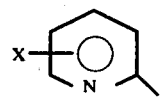

wherein X is H, or OH, provided only one of $R_1$ and $R_2$ is H, and provided when one of $R_1$ and $R_2$ is

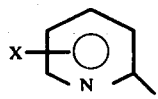

the other is H.

2. A compound as defined in claim 1 wherein R is alkyl.

3. A compound as defined in claim 2 having the name 9-hydroxy-2-methyl-4H-pyrido[1,2-a]pyrimidin-4-one.

4. A compound as defined in claim 2 having the name 9-hydroxy-2-methyl-4H-pyrido[1,2-a]pyrimidin-one, diethylamine salt.

5. A compound as defined in claim 2 having the name 9-hydroxy-2-methyl-4H-pyrido[1,2-a]pyrimidin-4-one, 2-amino-6-pyridinol salt.

6. A compound as defined in claim 2 having the name 9-hydroxy-2-methyl-4H-pyrido[1,2-a]pyrimidin-4-one, 2-aminopyridine salt.

7. A compound as defined in claim 2 having the name 9-hydroxy-2-methyl-4H-pyrido[1,2-a]pyrimidin-4-one, maleic acid salt.

8. A compound as defined in claim 2 having the name 9-hydroxy-2-methyl-4H-pyrido[1,2-a]pyrimidin-4-one, tartaric acid salt.

9. A compound as defined in claim 2 having the name 9-hydroxy-2-methyl-4H-pyrido[1,2-a]pyrimidin-4-one, salt with fumaric acid.

10. A compound as defined in claim 2 having the name 9-hydroxy-2-methyl-4H-pyrido[1,2-a]pyrimidin-4-one, salt with malic acid.

11. A compound as defined in claim 2 having the name 9-hydroxy-2-methyl-4H-pyrido[1,2-a]pyrimidin-4-one, n-butylamine salt.

12. A compound as defined in claim 2 having the name 9-hydroxy-2-methyl-4H-pyrido[1,2-a]pyrimidin-4-one, 2-amino-3-pyridinol salt.

13. A compound as defined in claim 2 having the name 9-hydroxy-2-propyl-4H-pyrido[1,2-a]pyrimidin-4-one.

14. A compound as defined in claim 2 having the name 9-hydroxy-2-propyl-4H-pyrido[1,2-a]pyrimidin-4-one, salt with p-toluenesulfonic acid.

15. A method of stimulating the central nervous system of mammals, which comprises administering a therapeutic amount of a compound as defined in claim 1.

16. A method of elevating the mood of animals, which comprises administering a therapeutic amount of a compound as defined in claim 1.

17. A compound of the structure

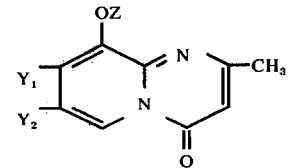

wherein Z is selected from the group consisting of o-bromobenzyl, allyl, 2,4-dichlorobenzyl, 2-bromo-4-chlorobenzyl, 2-phenethyl, cinnamyl, m-(trifluoromethyl)benzyl, o-cyanobenzyl, p-methoxybenzyl, p-(N,N-dimethylsulfamoyl)cinnamyl, 3-chloro-2-butenyl, p-(methylthio)benzyl, o-(carbomethoxy)benzyl, o-(trifluoromethyl)benzyl, p-(trifluoromethyl)benzyl, o-chlorobenzyl, 2-propynyl, or benzyl, $Y_1$ and $Y_2$ are hydrogen except in the case where Z is cinnamyl, $Y_1$ is hydrogen or methyl.

18. A pharmaceutical composition for use in stimulating the central nervous system comprising an effective amount of a compound as defined in claim 17 in combination with a pharmaceutically acceptable carrier.

19. A method for stimulating the central nervous system which comprises administering an effective amount of a composition as defined in claim 18.

* * * * *

UNITED STATES PATENT AND TRADEMARK OFFICE
CERTIFICATE OF CORRECTION

PATENT NO. : 4,022,897
DATED : May 10, 1977
INVENTOR(S) : Harry Louis Yale, et al.

It is certified that error appears in the above-identified patent and that said Letters Patent are hereby corrected as shown below:

Column 16, line 50, insert a hyphen after "4".

Column 21, line 34, after "0°" insert --to--.
Column 22, in the Table, column entitled Example, insert numbers --19-27--.
Column 26, line 55, "[2-a]" should read --[1,2-a]--.
Column 28, line 2, "solid," should read --solid.--

Signed and Sealed this second Day of August 1977

[SEAL]

Attest:

RUTH C. MASON
Attesting Officer

C. MARSHALL DANN
Commissioner of Patents and Trademarks